United States Patent [19]

Sayano et al.

[11] Patent Number: 5,217,490
[45] Date of Patent: Jun. 8, 1993

[54] ULTRAVIOLET LIGHT ABSORBING INTRAOCULAR IMPLANTS

[75] Inventors: Reizo Sayano, Montebello, Calif.; Eugene P. Goldberg, Tampa, Fla.

[73] Assignee: Kabi Pharmacia AB, Upsala, Sweden

[21] Appl. No.: 830,476

[22] Filed: Feb. 3, 1992

Related U.S. Application Data

[63] Continuation of Ser. No. 735,161, Jul. 23, 1991, abandoned, which is a continuation of Ser. No. 617,959, Nov. 26, 1990, abandoned, which is a continuation of Ser. No. 443,875, Nov. 30, 1989, abandoned, which is a continuation of Ser. No. 599,005, Apr. 11, 1984, abandoned.

[51] Int. Cl.$^5$ .............................................. A61F 2/16
[52] U.S. Cl. ......................................................... 623/6
[58] Field of Search ............................................. 623/6

[56] References Cited

U.S. PATENT DOCUMENTS

| | | | |
|---|---|---|---|
| 3,925,825 | 12/1975 | Richards et al. | 3/13 |
| 4,316,291 | 2/1982 | Severin | 3/13 |
| 4,390,676 | 6/1983 | Loshaek | 526/313 |
| 4,402,579 | 9/1983 | Poler | 3/13 |

FOREIGN PATENT DOCUMENTS

| | | | |
|---|---|---|---|
| 32835 | 7/1981 | European Pat. Off. | 3/13 |
| 1480492 | 7/1977 | United Kingdom | 3/13 |

OTHER PUBLICATIONS

Undated brochure. Pure Perspec CQ With UV Absorber—The American Revolution in Intraocular Lenses—Date unavailable.
Undated brochure. Pure Perspec CQ With UV Absorber— . . . exclusively from American Medical Optics—Date unavailable.
Undated brochure. Technical Report Series #14—Scientific Basis for the Selection of a UV Absorbing Intraocular Lens Material-Data unavailable.
Optical Radiation Corp. Literature; "New ORC UV400®: The First IOL Designed for UV Protection".
Surgidev Literature; "The Leiske Physioflex Style 10 Anterior Chamber Lens".
The Merck Index; "Tinuvin ® P." p. 1053, 8th edition 1968.
The Condensed Chemical Dictionary; "1,2,3-benzotriazole" p. 99, 9th Edition 1977.

Primary Examiner—Mark L. Bell
Assistant Examiner—Helene Klemanski
Attorney, Agent, or Firm—Poms, Smith, Lande & Rose

[57] ABSTRACT

Intraocular implants having optical lenses that are light, non-toxic, biocompatible, nonleachable in the presence of eye fluids and absorb at least 90% of the ultraviolet light in the 300-380 nm wavelength range but are transparent to most of the visible radiation. The intraocular implants will have a haptic for fixation in the posterior or anterior chamber of the eye. The optical lens has uniformly dispersed therein an ultraviolet light absorbing amount of 2-(hydroxy-lower alkylphenyl) benzotriazole which may be halogen substituted in the 4, 5, 6 or 7 positions.

6 Claims, 1 Drawing Sheet

Fig. 1.
Fig. 2.
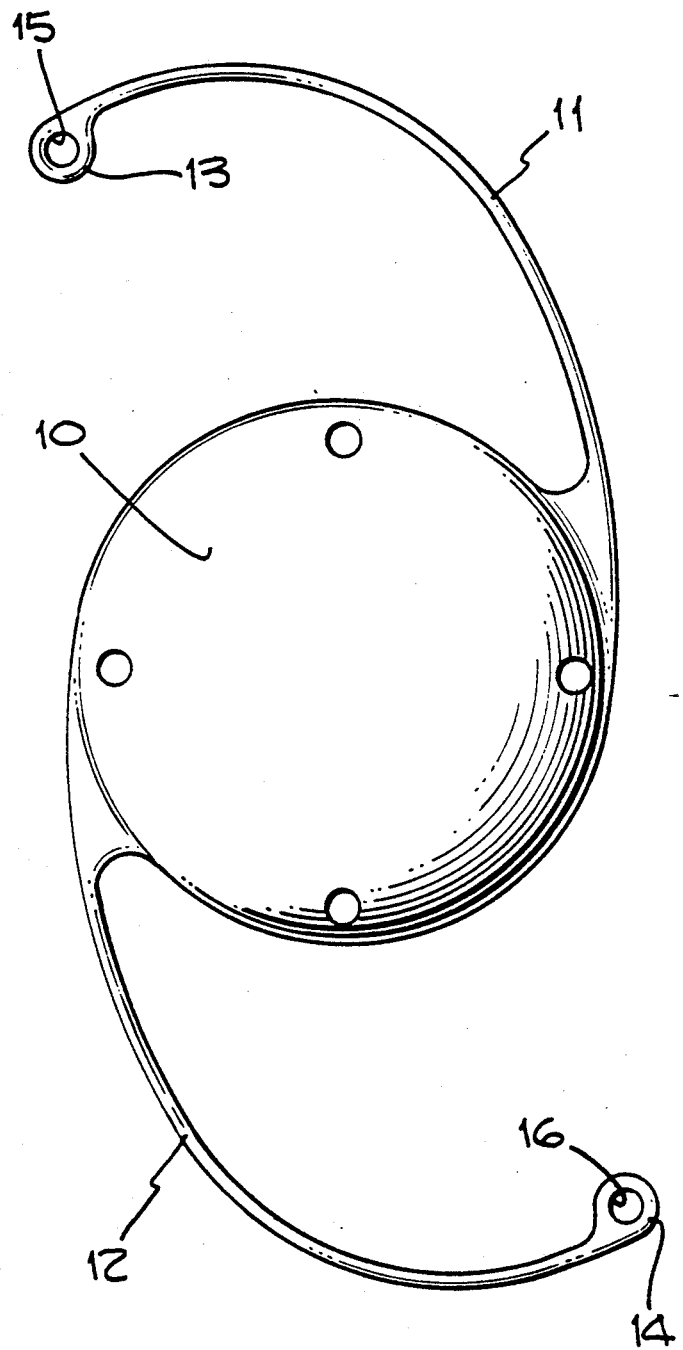
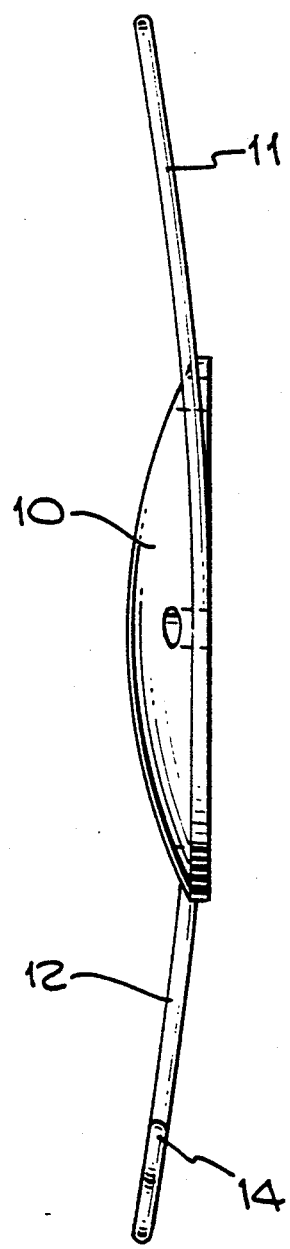

ULTRAVIOLET LIGHT ABSORBING INTRAOCULAR IMPLANTS

This is a continuation of copending application Ser. No. 07/735,161 filed on Jul. 23, 1991 now abandoned which is a continuation of application Ser. No. 07/617,959, filed on Nov. 26, 1990 now abandoned, which is a continuation of application Ser. No. 07/443,875 filed on Nov. 30, 1989, now abandoned, which is a continuation of application Ser. No. 06/599,005, filed Apr. 11, 1984, now abandoned.

BACKGROUND OF THE INVENTION

Certain injuries to the eye and certain diseases to the eye (e.g. cataracts) require surgical removal of the eye lens. Removal of the natural lenses of the eye is known as aphakia which must be corrected by the use of a corrective lens in order to restore vision. Generally, intraocular implants are used to correct aphakia and restore vision. These implants may be permanently placed in the anterior or posterior chamber of the eye. Intraocular implants have an optical lens and a haptic for fixation of the lens, by a surgeon, in the anterior or posterior chamber of the eye. However, even with the most suitable of lenses, vision is not as desirable as it should be for the aphakic individual since such lenses do not adequately compensate for certain changes in light transmission which occur in the absence of the natural human crystalline lens. The result is potential damage to the retina due to increased ultraviolet light transmission.

A considerable portion of incident light entering the eye is absorbed and only the unabsorbed or transmitted portion strikes the retina. Natural light encompasses the entire spectrum of wavelengths in the ultraviolet, visible and infrared radiation ranges. Various artificial light sources also contain many wavelengths.

The crystalline lens of the eye preferentially absorbs a substantial portion of ultraviolet radiation. Accordingly, it is desirable that the lenses of intraocular implants for aphakic individuals, absorb at least 90% of light in the 300 to about 380 nm range but transmit most of the light in the visible spectrum. In addition, intraocular implant lenses are preferably made of a thermoplastic polymer and optically clear, inert to the eye, biocompatible and have a specific gravity of less than about 1.7.

Polymethylmethacrylate sometimes referred to as "PMMA", and various copolymers thereof, have the desired properties discussed above and have been used to make intraocular lenses as well as haptics. PMMA has physical properties which permit it to be formed into introcular optic lenses that are relatively thin in cross section and, because of PMMA's relatively low specific gravity, about 1.4 or lower, such lenses are relatively comfortable in the eye. However, PMMA, and copolymers thereof have a serious disadvantage in that they are substantially transparent to ultraviolet radiation which, if transmitted to the retina, can cause eye injury. To avoid this disadvantage intraocular lenses have been fabricated from glass which can absorb ultraviolet radiation. However, compared to PMMA which is relatively easy to machine, glass lenses of relatively thin cross sections are much more difficult to produce. Furthermore since glass lenses have a specific gravity of 2.5 or higher such lenses are relatively heavy and therefore mitigate against the use of such lenses in aphakic individuals.

To overcome the disadvantage of PMMA lenses to ultraviolet radiation transmission, natural and synthetic crystals have also been used to construct intraocular lenses. U.S. Pat. No. 4,079,470 discloses a chemically durable optical implant lens formed from a low density natural or synthetic crystal, such as Corundium, Sapphire, Ruby, Sircon, Strontium, Diamond or Anatase. Because of the ability of these materials to absorb ultraviolet radiation such crystals provide an advantage over lenses made from PMMA. However, as with glass, it is more difficult to produce intraocular lenses which have relatively thin cross sections from these crystals. In general, lenses made from such crystals must be considerably thicker than lenses made from PMMA. Crystal lenses like glass lenses, are relatively heavy due to their high specific gravity, about 3.5 or higher, and larger size. Consequently, such crystal lenses are also heavier than the natural lenses of the human eye, and may also impose an undesirable strain to the eye. For these and other reasons, intraocular lenses made from PMMA, tend to be preferred over synthetic or natural crystals and glass lenses.

There is a need for an intraocular implant having an optical lens which is nontoxic, biocompatible and which absorbs a high percentage of ultraviolet light and does not contain leachable or potentially harmful ultraviolet light absorbing additives.

There is also a need for an intraocular optical lens material made of a thermoplastic polymer which is strong, ductile and easily machined or molded into thin sections and having a specific gravity less than about 1.7 and preferably about 1.4 or lower, which is chemically inert and stable, is biocompatible, nonleachable by fluids of the eye, is optically clear and absorbs a major portion of harmful ultraviolet light.

SUMMARY OF THE INVENTION

In accordance with the present invention, novel intraocular implants are provided which have optical lenses that are light, non-toxic, biocompatible, non-leachable in the presence of eye fluids and absorb at least 90% of the ultraviolet light in the 300–380 nm wavelength range but are transparent to most of the visible radiation. The intraocular implants will have a haptic for fixation in the posterior or anterior chamber of the eye.

The haptics of the intraocular implant may have a variety of shapes and can be made of a variety of thermoplastic polymers which are biocompatible, chemically inert, light weight (i.e. have a specific gravity of less than 1.7) strong, tough and flexible and are inert to the fluids in the eye. Such haptics may be made of polypropylene, aromatic polycarbonates, aromatic polyesters, aromatic polyimides, aromatic polyethersulfones, etc.

The intraocular lens of the present invention will have optically finished front and back surfaces and a shape and size approximating the human lens and will be made of an optical quality thermoplastic polymer having a specific gravity of less than about 1.7, said thermoplastic polymer having uniformly distributed throughout an ultraviolet light absorbing effective amount in the 300–380 nm range of 2-(hydroxy, lower alkylphenyl) benzotriazole which, optionally, may be halogen (e.g. chlorine) substituted in one or more of the 4, 5, 6 or 7 positions.

The intraocular lenses are formulated so that the ultraviolet radiation absorbing substance is nonleachable in the eye from said thermoplastic polymer. The ultraviolet absorbing substance is also substantially nontoxic. The amount of ultraviolet radiation absorbing substance is small enough so the lens is transparent to most of visible radiation but great enough to render the lens absorbent to at least 90% of the ultraviolet radiation of sunlight in the 300 to 380 nm range.

The critical requirement of the invention is that the ultraviolet radiation absorber be effective at low concentrations and be nonleachable or nonextractable from the solid thermoplastic polymer in the eye.

The solid thermoplastic polymer may be polymethylethacrylate, and copolymers thereof with monomers such as methylacrylate, hydroxyethylmethacrylate, ethyl acrylate, butyl acrylate, mixtures thereof, and the like. The particular monomer, or combination of monomers, as well as other additives, such as cross-linking agents and polymerization catalysts, used to form the various polymeric systems are known in the art. Other thermoplastic polymers well suited to be used in both the lens and haptic include aromatic polycarbonates such as lexan available from General Electric; polysulfones such as Udel P-1700 available from Union Carbide; and polyetherimides such as Ultem available from General Electric.

The ultraviolet light absorbing compounds useful in the present invention are stable, inert, biocompatible, water insoluble, non-leachable and strongly ultraviolet 5 light absorbing compounds based on the benzotriazole structure and include 2-(3',5'-ditertiary butyl-2'-hydroxy phenyl) benzotriazole, 2-(3'-tertiary-butyl-5'-methyl-2'-hydroxy phenyl-5-chlorobenzotriazole and 2-(2'-hydroxy-5'methylphenyl)benzotriazole.

In the formulation and production of the lenses of this invention, the amount of the ultraviolet radiation absorber will be sufficient to absorb at least 90% of the ultraviolet radiation of sunlight in the 300–380 nm range but will not prevent the lens from being transparent to a substantial part of the visible spectrum.

The lenses of this invention may be easily produced using standard procedures such as lathe cutting, injection molding, compression molding and casting.

The ultraviolet light absorbing compound may be uniformly distributed through the thermoplastic polymer by the polymerization of the monomers in the presence of the ultraviolet radiation absorbing compound. Alternatively, the ultraviolet light absorbing compound may be compounded with the thermoplastic polymer prior to extrusion or molding. The amount of the absorbing compound is preferably from about 0.01 to about 5 parts by weight per 100 parts by weight of the polymer. The ultraviolet light-absorbing compounds of this invention are inert and do not adversely affect the polymerization of the monomers used to produce the thermoplastic polymers, or their processing by molding or extrusion.

BRIEF DESCRIPTION OF THE DRAWINGS

FIG. 1 is an illustration in plan view of an intraocular implant for implantation in the anterior chamber of the eye.

FIG. 2 is a side view of the intraocular implant of FIG. 1.

DESCRIPTION OF THE PREFERRED EMBODIMENTS

The intraocular implant of the present invention will have a generally circular optic lens 10 as shown in FIGS. 1 and 2 which is made of a thermoplastic polymer having uniformly distributed therethrough an ultraviolet light absorbing amount of 2-(hydroxy-lower alkylphenyl) benzotriazole which may be halogen substituted in the 4, 5, 6 or 7 positions. The amount of benzotriazole distributed throughout the polymer is preferably from about 0.01 to about 5 parts by weight of the thermoplastic polymer.

The ultraviolet light absorbing substance may be mixed with the monomers and then the monomers polymerized or by compounding with the thermoplastic polymer prior to extrusion or molding.

In addition to the optic lens 10, the intraocular implant of the present invention also have haptics connected to the optic lens for positioning and fixing the implant in either the anterior or posterior chamber of the eye. In the embodiment of this invention shown in FIGS. 1 and 2, haptic 11 and haptic 12 are resilient so that they can be compressed when being placed in the eye but will spring out when the implant is in the correct position so that positioning element 13 of haptic 11 and positioning element 14 of haptic 12 will contact and be seated in the groove of the anterior chamber of the eye. Aperture 15 and aperture 16 are provided for grasping with forceps.

The haptics may be made of any thermoplastic polymer which is strong and lightweight, chemically inert and biocompatible. The haptic may be made of the same material as the lens, e.g. polysulfone, polycarbonate, etc., or may be different, e.g. a PMMA optic with polypropylene haptic.

TEST RESULTS

Example 1

Three fine dispersions of 200 micro-grams of each of the following ultraviolet light absorbing compounds in a 0.9% saline solution were made: 2-(3',5'-ditertiarybutyl-2'-hydroxy phenyl) benzotriazole (hereinafter DHP), 2-(2'-hydroxy-5'-methylphenyl) benzotriazole (hereinafter HMP), and 2-(3'-tertiary-butyl-5'-methyl-2'-hydroxy phenyl-5-chlorobenzo-triazole (hereinafter TMP). Each of the three saline solutions were injected, respectively, into the anterior chamber of the eyes of three rabbits. This amount is the equivalent of 1 weight % of ultraviolet light absorbing compound in a 20 mg. lens.

No adverse reactions were noted. The animals were followed for one week and the eyes were normal and tissue histology was normal. This test demonstrates the non-toxic biocompatible properties of the ultraviolet light absorbing compounds.

Example 2

100 parts by weight of polysulfone (Udel P-1700) pellets were mixed with 8 parts by weight of TMP powder. The mixture was extruded into a rod at 550° F. to 600° F. and then cut into discs of about 1.0 mm thickness. The discs absorbed over 95% of the ultraviolet light in the 300 to 400 nm region and had a sharp cut-off of absorption between 400 and 420 nm.

Example 3

100 parts by weight of polysulfone (Udel P-1700) pellets were mixed with 10 parts by weight of DHP powder. This mixture was compression molded into a 1 mm thick sheet which absorbed over 95% of the ultraviolet light in about the 300 to 400 nm region and had a sharp cut-off of absorption in the 400 to 420 nm region (there was 5% transmission at 403 nm and 70% at 420 nm).

Example 4

A sheet, 2.95 mm thick, was made having 100 parts by weight of PMMA and 10 parts by weight of DHP. The sheet absorbed more than 95% of ultraviolet light in the 300–400 nm region and had a sharp cut-off of absorption in about the 405 to 430 nm range (there was less than 5% trans mission at 405 nm and about 90% transmission at 430 nm).

Example 5

A sheet, ⅛ inch thick, was made having 100 parts by weight of PMMA and 10 parts by weight of HMP. This sheet absorbed over 95% of the ultraviolet light between 300 and 400 nm with a sharp cut-off of absorption at about 400 nm (there was about 5% transmission at 400 and over 90% transmission at about 425 nm).

Example 6

The PMMA containing HMP material used in Example 5 was used in this example. Four samples of the material were extracted in four (4) different media for one (1) hour at 121° C.
1. Sodium chloride
2. Ethanol in sodium chloride
3. Polyethylene glycol
4. Cottonseed oil Two rabbits were used for each extract. Exactly 0.2 ml of test material extract was injected intracutaneously in ten (10) sites on the right side of each animal and ten (10) injections of 0.2 ml of extracting medium were placed into the left side of each animal. The degree of erythema and edema of the two sides were compared 1, 2 and 3 days after the injection to determine the degree of tissue reaction.

There were no significant signs of erythema nor edema due to the intracutaneous injection of extraction of the PMMA material as compared to injections of the extraction mediums. Therefore, an extract of PMMA material does not result in erythema or edema 72 hours after intracutaneous injection. This test demonstrates the non-toxic and nonleachable properties of the ultraviolet light absorbing additive.

Example 7

Four (4) grams of material having the same composition as used in Example 6 were cut into 11 pieces approximately 1.016 cm square and 0.3 cm thick (37.07 $cm^2$ total surface area for each 4 grams). The materials were cleaned and sterilized. The 4 grams were then incubated at 90° C. in 20 ml of saline (1 gr for each 5 ml of saline or 1 $cm^2$ surface area for each 0.55 ml of saline).

After 1.5 weeks of 90° C., the material was removed and the ultraviolet absorbace of the extract measured. The concentration of the absorber in the extract was determined from the absorbance.

The absorbance of pure saline subtracted from the absorbance of the extract of the ultraviolet absorbing PMMA, was always less than 0.004 between wavelengths of 300 and 400 nm. Since the ultraviolet absorber strongly absorbs ultraviolet radiation and is stable above 140° C., it would have been detected by this method. Therefore, there was no significant leaching of ultraviolet absorber, since there was negligible absorbance of the ultraviolet filtering PMMA extract.

Example 8

Intraocular implants of PMMA containing 0.1 weight percent of HMP were implanted in the anterior chamber of rabbits. No toxic or adverse behavior was observed after one year. There was also one explanted lens which showed no change in ultraviolet light absorbing properties.

We claim:

1. An intraocular lens for implantation into a human eye to replace the natural lens, said intraocular lens being adapted to provide absorption of ultraviolet light and transmission of visible light which mimics said natural lens, said intraocular lens comprising an optic lens which consists essentially of an optical quality solid thermoplastic polymer having a specific gravity of less than about 1.7, said polymer having uniformly distributed therein an ultraviolet absorber selected from the group of benzotriazoles consisting of 2-(3',5'-ditertiary butyl-2'-hydroxy phenyl-5-chlorobenzotriazole and 2-(2'-hydroxy-5'-methyl-phenyl)benzotriazole said ultraviolet absorber being present in said optic lens in an amount sufficient to absorb at least 90 percent of said ultraviolet light in the 300 to 380 nm range while transmitting substantially all of said visible light.

2. An intraocular lens according to claim 1 wherein said thermoplastic polymer is selected from the group consisting of polymethylmethacrylate and copolymers thereof, aromatic polycarbonate, aromatic polysulfone and aromatic polyetherimide.

3. An intraocular lens according to claim 2 wherein said thermoplastic polymer is polymethylmethacrylate.

4. An intraocular lens according to claim 3 wherein said ultraviolet absorber is 2-(3', 5'-ditertiary butyl-2'-hydroxy phenyl) benzotriazole.

5. An intraocular lens according to claim 3 wherein said ultraviolet absorber is 2-(2'-hydroxy-5'-methyl phenyl) benzotriazole.

6. An intraocular lens according to claim 3 wherein said ultraviolet absorber is 2-(3'-tertiary-butyl-5'-methyl-2'-hydroxy phenyl)-5-chlorobenzo-triazole.

* * * * *